United States Patent
Ferguson et al.

(10) Patent No.: US 8,246,893 B2
(45) Date of Patent: Aug. 21, 2012

(54) METHOD OF MOLDING A MICRONEEDLE

(75) Inventors: Dennis E. Ferguson, Mahtomedi, MN (US); Satinder K. Nayar, Woodbury, MN (US); Donald L. Pochardt, Hastings, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/049,448

(22) Filed: Mar. 16, 2011

(65) Prior Publication Data

US 2011/0163479 A1    Jul. 7, 2011

Related U.S. Application Data

(62) Division of application No. 11/720,480, filed as application No. PCT/US2005/044121 on Dec. 7, 2005, now Pat. No. 8,088,321.

(60) Provisional application No. 60/634,319, filed on Dec. 7, 2004.

(51) Int. Cl.
*B29C 45/56* (2006.01)
*B29C 69/02* (2006.01)

(52) U.S. Cl. ........................ 264/443; 264/478

(58) Field of Classification Search ............ 264/442, 264/443, 478
See application file for complete search history.

(56) References Cited

U.S. PATENT DOCUMENTS

| | | |
|---|---|---|
| 3,072,122 A | 1/1963 | Rosenthal |
| 3,678,150 A | 7/1972 | Szumski et al. |
| 3,964,482 A | 6/1976 | Gerstel et al. |
| 4,381,963 A | 5/1983 | Goldstein et al. |
| 4,489,033 A | 12/1984 | Uda et al. |
| 4,515,543 A | 5/1985 | Hamner |
| 4,793,954 A | 12/1988 | Lee et al. |
| 5,141,677 A | 8/1992 | Fogarty |
| 5,152,917 A | 10/1992 | Pieper et al. |
| 5,160,823 A | 11/1992 | Bennin et al. |
| 5,250,023 A | 10/1993 | Lee et al. |
| 5,256,360 A | 10/1993 | Li |
| 5,342,737 A | 8/1994 | Georger, Jr. et al. |
| 5,376,317 A | 12/1994 | Maus et al. |
| 5,543,108 A | 8/1996 | Bacher et al. |
| 5,591,139 A | 1/1997 | Lin et al. |
| 5,611,806 A | 3/1997 | Jang |
| 5,645,977 A | 7/1997 | Wu et al. |
| 5,657,516 A | 8/1997 | Berg et al. |
| 5,658,515 A | 8/1997 | Lee et al. |
| 5,879,326 A | 3/1999 | Godshall et al. |
| 5,983,136 A | 11/1999 | Kamen |
| 6,021,559 A | 2/2000 | Smith |
| 6,050,988 A | 4/2000 | Zuck |
| 6,076,248 A | 6/2000 | Hoopman et al. |
| 6,129,540 A | 10/2000 | Hoopman et al. |

(Continued)

FOREIGN PATENT DOCUMENTS

DE    102 46 942    4/2004

(Continued)

OTHER PUBLICATIONS

Battenfeld Microsystem, Injection Molding Technology, date unknown, in English, pp. 1-9.

(Continued)

*Primary Examiner* — Jill Heitbrink (57) ABSTRACT

A method of molding a microneedle using a mold apparatus that includes the use of high frequency acoustic energy, such as ultrasonic energy.

13 Claims, 7 Drawing Sheets

U.S. PATENT DOCUMENTS

| | | | |
|---|---|---|---|
| 6,132,755 A | 10/2000 | Eicher et al. |
| 6,248,281 B1 | 6/2001 | Abe et al. |
| 6,256,533 B1 | 7/2001 | Yuzhakov et al. |
| 6,312,612 B1 | 11/2001 | Sherman et al. |
| 6,322,808 B1 | 11/2001 | Trautman et al. |
| 6,331,266 B1 | 12/2001 | Powell et al. |
| 6,334,856 B1 | 1/2002 | Allen et al. |
| 6,361,733 B1 | 3/2002 | Eicher et al. |
| 6,379,324 B1 | 4/2002 | Gartstein et al. |
| 6,451,240 B1 | 9/2002 | Sherman et al. |
| 6,454,755 B1 | 9/2002 | Godshall |
| 6,503,231 B1 | 1/2003 | Prausnitz et al. |
| 6,511,463 B1 | 1/2003 | Wood et al. |
| 6,532,386 B2 | 3/2003 | Sun et al. |
| 6,533,949 B1 | 3/2003 | Yeshurun et al. |
| 6,551,849 B1 | 4/2003 | Kenney |
| 6,565,532 B1 | 5/2003 | Yuzhakov et al. |
| 6,591,124 B2 | 7/2003 | Sherman et al. |
| 6,595,947 B1 | 7/2003 | Mikszta et al. |
| 6,603,998 B1 | 8/2003 | King et al. |
| 6,605,332 B2 | 8/2003 | Calhoun et al. |
| 6,652,478 B1 | 11/2003 | Gartstein et al. |
| 6,663,820 B2 | 12/2003 | Arias et al. |
| 6,686,299 B2 | 2/2004 | Montemagno et al. |
| 6,713,291 B2 | 3/2004 | King et al. |
| 6,743,211 B1 | 6/2004 | Prausnitz et al. |
| 6,770,480 B1 | 8/2004 | Canham |
| 6,797,276 B1 | 9/2004 | Glenn et al. |
| 6,835,184 B1 | 12/2004 | Sage et al. |
| 6,881,203 B2 | 4/2005 | Delmore et al. |
| 6,899,838 B2 | 5/2005 | Lastovich |
| 6,908,453 B2 | 6/2005 | Fleming et al. |
| 6,931,277 B1 | 8/2005 | Yuzhakov et al. |
| 2001/0030382 A1 | 10/2001 | Lajza et al. |
| 2002/0045859 A1 | 4/2002 | Gartstein et al. |
| 2002/0053756 A1 | 5/2002 | Powell et al. |
| 2002/0082543 A1 | 6/2002 | Park et al. |
| 2002/0095134 A1 | 7/2002 | Pettis et al. |
| 2002/0138049 A1 | 9/2002 | Allen et al. |
| 2002/0169416 A1 | 11/2002 | Gonnelli et al. |
| 2002/0177858 A1 | 11/2002 | Sherman et al. |
| 2002/0198509 A1 | 12/2002 | Mikszta et al. |
| 2003/0045837 A1 | 3/2003 | Delmore et al. |
| 2003/0078549 A1 | 4/2003 | Stupar et al. |
| 2003/0095582 A1 | 5/2003 | Ackley |
| 2003/0135166 A1 | 7/2003 | Gonnelli |
| 2003/0135167 A1 | 7/2003 | Gonnelli |
| 2003/0135201 A1 | 7/2003 | Gonnelli |
| 2003/0148401 A1 | 8/2003 | Agrawal et al. |
| 2003/0199810 A1 | 10/2003 | Trautman et al. |
| 2004/0049150 A1 | 3/2004 | Dalton et al. |
| 2004/0060902 A1 | 4/2004 | Evans et al. |
| 2004/0176732 A1 | 9/2004 | Frazier et al. |
| 2005/0025778 A1 | 2/2005 | Cormier et al. |
| 2005/0065463 A1 | 3/2005 | Tobinaga et al. |
| 2005/0106226 A1 | 5/2005 | Cormier et al. |
| 2005/0118388 A1 | 6/2005 | Kingsford |
| 2005/0137525 A1 | 6/2005 | Wang et al. |
| 2005/0261631 A1 | 11/2005 | Clarke et al. |
| 2008/0275400 A1 | 11/2008 | Ferguson ............... 604/173 |

FOREIGN PATENT DOCUMENTS

| | | |
|---|---|---|
| DE | 102 46 942 A1 | 4/2004 |
| EP | 1 088 642 A | 4/2001 |
| EP | 1 287 847 A | 3/2003 |
| JP | 01 182016 A | 7/1989 |
| JP | 01 218813 A | 9/1989 |
| JP | 04 176623 A | 6/1992 |
| JP | 2004-114552 | 4/2004 |
| WO | WO 96/10630 | 4/1996 |
| WO | WO 00/45798 | 8/2000 |
| WO | WO 00/74766 | 12/2000 |
| WO | WO 01/36037 | 5/2001 |
| WO | WO 2004/024416 A | 3/2004 |
| WO | WO 2004/106029 A | 12/2004 |
| WO | WO 2005/051455 | 6/2005 |
| WO | WO 2005/082596 A | 9/2005 |

OTHER PUBLICATIONS

Heckele, M. et al.; "Topical Review—Review on micro moldling of thermoplastic polymers"; Journal of Micromechanics and Microengineering; vol. 14; (2004) pp. R1-R14.

Daddona, Current Opinion in Drug Discovery and Development 1999 2(2);168-171.

Kaushik et al. Anesthesia Analg., 2001, 92, 502-504.

Henry et al. J. Pharm.Sci., 1998, 87,8,922-925.

Mcallister et al. Annual Review of Biomedical Engineering, 2000, 2, 289-313.

Mcallister et al. Proceed. Int'l. Symp. Control Release of Bioactive Material, 26, (1999), CRS, 192-193.

Griss et al. IEEE 2002, pp. 467-470.

Weber et al. Proceedings of SPIE vol. 2879, p. 156.

Edwards, Proceedings of SPIE vol. 4177.

"Development of Plastic Microneedles for Transdermal Interfacing Using Injection Molding Techniques", Trichur et al., Micro Total Analysis Systems, 2002, vol. 1, 395-397.

Martyn M T et al.: "Micromoulding: consideration of processing effects on medical materials" ANTEC 2003 Pastics Annual Technical Conference, vol. 3, 2003, pp. 2582-2586. XP007900398.

Battenfeld Spritzgiesstechnik: "Microsystem, Catalogue Jun. 2005" XP007900399.

Cui A et al.: "Method of improving the quality of moulded plastics by ultrasonic vibration" Rapra Abstracts, Rapra Technology LTD., Shrewsbury GB vol. 31, No. 5, May 1, 1994 p. 189 XP00446148.

Ibar J. P.: :Improving molding through melt-flow oscillation Modern Plastics International, Mcgraw-Hill, Inc Lausanne, CH vol. 25, No. 1 Jan. 2005 pp. 72-74, 77, XP0000521251.

Henry et al.: "Micromachined Needles for the Transdermal Delivery of Drugs", Georgia Institute of Technology, 1998, pp. 494-498.

Martyn M T et al.: "Micromoulding: consideration of processing effects on medical materials" ANTEC 2003 Plastics Annual Technical Conference, vol. 3, 2003, pp. 2582-2586. XP007900398.

Mcallister et al.: "Solid and Hollow Microneedles for Transdermal Protein Delivery", Proceed. Int'l. Symp. Control Release of Bioactive Material, 26. (1999), Controlled Release Society, Inc., pp. 192-193.

METHOD OF MOLDING A MICRONEEDLE

CROSS-REFERENCE TO RELATED APPLICATIONS

The present application is a divisional application of prior application Ser. No. 11/720,480, filed May 30, 2007 now U.S. Pat. No. 8,088,321 which was a national stage filing under 35 U.S.C. 371 of PCT/US2005/044121, filed Dec. 7, 2005, which claims priority to 60/634,319, filed Dec. 7, 2004, the disclosures of which are incorporated by reference in their entirety herein.

FIELD

The present invention relates to methods of molding microneedles. In one aspect, the present invention relates to methods of molding microneedle arrays.

BACKGROUND

Only a limited number of molecules with demonstrated therapeutic value can be transported through the skin, even with the use of approved chemical enhancers. The main barrier to transport of molecules through the skin is the stratum corneum (the outermost layer of the skin).

Devices including arrays of relatively small structures, sometimes referred to as microneedles or micro-pins, have been disclosed for use in connection with the delivery of therapeutic agents and other substances through the skin and other surfaces. The devices are typically pressed against the skin in order to pierce the stratum corneum such that the therapeutic agents and other substances can pass through that layer and into the tissues below.

Molding processes to prepare microneedles and microneedle arrays have been previously disclosed, but microneedles are very fine structures that can be difficult to prepare in a polymeric molding process and the known microneedle molding processes all have certain disadvantages.

SUMMARY OF THE INVENTION

The present invention provides, among other things, an improved molding process for preparing microneedle arrays comprising a combination of injection and compression molding processes. The ability to reproduce the mold shape in the final molded part, reliably produce microneedles of a consistent height, and produce microneedle arrays in an economical fashion are among the desirable features of this invention. In one embodiment, this invention is particularly suitable for molding microneedles made from tough engineering grade plastics.

In one embodiment, the present invention is a method of molding a microneedle using a mold apparatus that comprises a mold insert having the negative image of at least one microneedle, a compression core, sidewalls having an injection gate, and a mold housing configured to allow a reciprocal motion between the mold insert and the compression core. The mold apparatus has an open position and a closed position. The mold apparatus is placed in the closed position and polymeric material is injected through the injection gate into the closed mold apparatus. The injected polymeric material is compressed between the mold insert and the compression core by a reciprocal motion between the compression core and the mold insert. The mold is opened and a molded microneedle is removed from the mold.

In another embodiment, the present invention is a method of molding a microneedle using a mold apparatus that comprises a mold insert having the negative image of at least one microneedle, a compression core, and a mold housing configured to allow a reciprocal motion between the mold insert and the compression core. The mold apparatus has an open position and a closed position. The mold insert is heated to a temperature of greater than or equal to 200° F. (93.3° C.). The mold apparatus is placed in the closed position and polymeric material is injected into the closed mold apparatus. The injected polymeric material is compressed between the mold insert and the compression core by a reciprocal motion between the compression core and the mold insert. The mold is opened and a molded microneedle is removed from the mold.

In another embodiment, the present invention is a method of molding a microneedle using a mold apparatus that comprises a mold insert having the negative image of at least one microneedle, a compression core, and a mold housing configured to allow a reciprocal motion between the mold insert and the compression core. The mold apparatus has an open position and a closed position. The mold apparatus is placed in the closed position and polymeric material is injected into the closed mold apparatus. The polymeric material is characterized by a melt-flow index greater than about 5 g/10 minutes when measured by ASTM D1238 at conditions of 300° C. and 1.2 kg weight. The injected polymeric material is compressed between the mold insert and the compression core by a reciprocal motion between the compression core and the mold insert so that the negative image of the at least one microneedle is substantially completely filled with the injected polymeric material. The mold is opened and a molded microneedle is removed from the mold.

In another embodiment, the present invention is a method of molding a microneedle using a mold apparatus that comprises a mold insert having the negative image of at least one microneedle. The mold apparatus has an open position and a closed position. Acoustic energy having a frequency greater than about 5,000 Hz is applied to the mold apparatus. The mold apparatus is placed in the closed position and polymeric material is injected into the closed mold apparatus. The mold is opened and a molded microneedle is removed from the mold. In one embodiment, the acoustic energy is ultrasonic energy.

In another embodiment, the present invention is a method of molding a microneedle using a mold apparatus that comprises a mold insert having the negative image of at least one microneedle, a compression core, and a mold housing configured to allow a reciprocal motion between the mold insert and the compression core. The mold apparatus has an open position and a closed position. The mold apparatus is placed in the closed position and polymeric material is injected into the closed mold apparatus. The injected polymeric material is compressed between the mold insert and the compression core by a reciprocal motion between the compression core and the mold insert. The mold is opened and a molded microneedle is removed from the mold.

The invention will be further understood by those skilled in the art upon consideration of the remainder of the disclosure, including the Detailed Description and the appended claims.

BRIEF DESCRIPTION OF THE DRAWINGS

Preferred embodiments of the invention will now be described in greater detail below with reference to the attached drawings, wherein.

DETAILED DESCRIPTION

Figure 1:
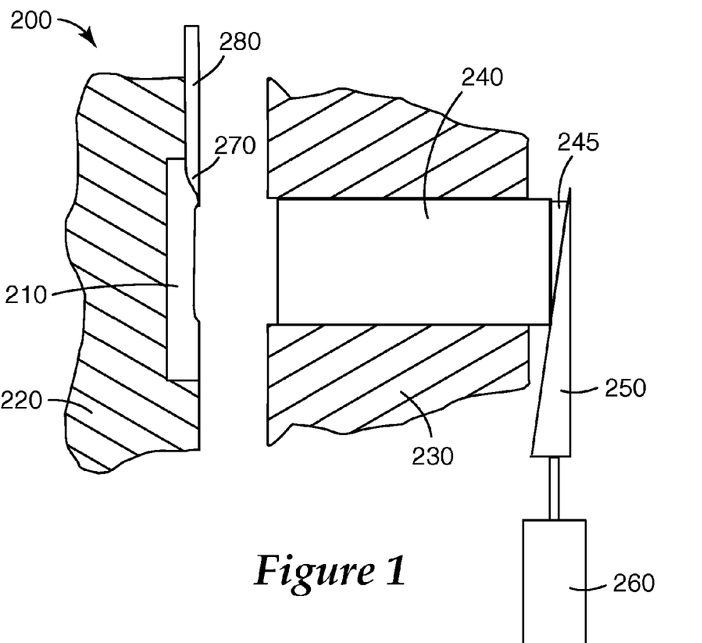
FIG. 1 is a schematic cross-sectional view of one embodiment of a mold apparatus in an open position.

One embodiment of the method of molding a microneedle is shown in FIGS. 1 to 4. FIG. 1 shows a mold apparatus in the open position. The mold apparatus comprises a mold housing formed from a first mold member 220 and a second mold member 230. The first mold member 220 partially surrounds a mold insert 210 which has the negative image of at least one microneedle. In the illustrated embodiment, the mold insert 210 has the negative image of a microneedle array. The second mold member 230 partially surrounds a compression core 240, which is conventionally in the form of a piston. The mold housing is configured to allow a reciprocal motion between the mold insert 210 and the compression core 240. A wedge 250 that is driven by a hydraulic cylinder 260 transmits force to the compression core 240 via a core-wedge connection 245. The connection 245 is shown as a separate piece, but may be integrally formed as part of the compression core 240 or it may be any conventional linkage that can transmit mechanical force based on the motion of the wedge 250. An input line 280 is used to input molten polymeric material through an injection gate 270 and into the mold cavity that is formed when the mold apparatus is in the closed position.

Figure 2:
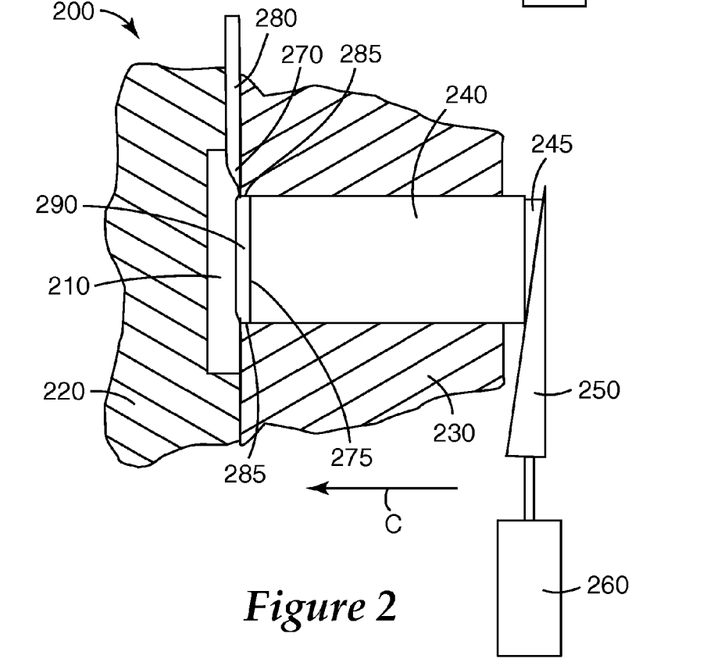
FIG. 2 is a schematic cross-sectional view of one embodiment of a mold apparatus in a closed position.

The mold apparatus 200 is shown in the closed position in FIG. 2. The arrow, identified as "C", indicates the direction of motion of the right portion of the apparatus which comprises the second mold member 230, compression core 240, and wedge 250, although it should be noted the orientation of the mold apparatus as shown is arbitrary and may be rotated or inverted as desired. The left portion of the mold apparatus comprises the first mold member 220 and the mold insert 210. In the closed position, the left and right portions of the apparatus rest against each other by their joint face, allowing the polymeric material to be injected into the mold apparatus. The left portion and the right portion are spaced apart in the open position, making it possible to remove the molded microneedle from the mold.

The mold apparatus 200 in the closed position defines a mold cavity 290. The shape of the mold cavity 290 is defined on one major surface by the mold insert 210 and on an opposing major surface by the near end 275 of the compression core 240. The second mold member 230 and the mold insert 210 also define sidewalls 285. The injection gate 270 is an opening on the sidewalls 285. In one embodiment, the sidewalls 285 may be formed entirely by the mold insert 210, that is, the near end 275 of the compression core 240 would be flush with the ends of the second mold member 230. In another embodiment, the sidewalls 285 may be formed entirely by the second mold member 230, that is, the right hand face of the mold insert would be flush with the surface of the first mold member 220. It should be understood that the sidewalls 285 may be formed by any combination of the above descriptions and need not be a separate piece, but are rather intended to define the sides of the mold cavity 290 formed by the interrelation of all of the parts of the mold apparatus. Other designs are equally suitable so long as the mold apparatus defines a mold cavity which may be filled with molten polymeric material under pressure.

With the mold apparatus in the closed position, molten polymeric material is injected through the input line 280 and injection gate 270 to partially fill the mold cavity 290. Once the mold cavity 290 is partially filled to a desired amount, then the hydraulic cylinder 260 moves the wedge 250 in the direction of the arrow identified as 'A' in FIG. 3 to place the mold apparatus 200 in a compressed position. Movement of the wedge 250 causes corresponding movement of the compression core 240 in the direction of the arrow identified as 'B', that is, there is a reciprocal motion between the compression core 240 and the mold insert 210. The molten polymeric material is thus compressed within the mold cavity 290 thereby aiding in filling the negative image of the microneedle array in the mold insert 210. The mold apparatus is subsequently opened, as shown in FIG. 4, and the arrows show the direction of motion of the various parts (compression core 240, wedge 250, second mold member 230) returning to their open positions. A molded microneedle array 295 is then ejected from the open mold apparatus by any conventional method, such as with the use of ejector pins (not shown). The cycle shown in FIGS. 1 to 4 may subsequently be repeated as desired to produce multiple parts.

In one embodiment the mold apparatus may be configured so as to have multiple, individual mold cavities. Each mold cavity has a negative image of a microneedle array, such that the result of a single cycle of injection and compression produces multiple microneedle arrays. The number of individual mold cavities may be, for example, 4 or more, often 8 or more, and in some instances 32 or more. The injection pressure with which the molten polymeric material is injected into the mold cavities may be adjusted accordingly depending on the shape, size, and number of cavities being filled. The compressive force to the individual mold cavities may be provided by a single device, such as a hydraulic cylinder, which is configured so as to distribute the compressive force evenly across the different cavities. Alternatively, more than one device may be used to supply compressive force. For example, a hydraulic cylinder may be provided to supply compressive force to each mold cavity, to every two mold cavities, or to every 4 mold cavities.

In one embodiment the mold insert 210 is heated to a temperature of greater than or equal to about 200° F. (93.3° C.), and sometimes to a temperature greater than or equal to 250° F. (121° C.). Heating of the mold insert may be desirable to aid in flow of the injected polymeric material into the fine structures of the mold insert. In particular, heating of the mold insert may allow for use of reduced compressive forces and/or may decrease cycle times. In a preferred embodiment, the temperature of the mold insert 210 is held substantially constant. The mold insert is preferably maintained at or below the temperature at which the polymeric material will form a part with sufficient rigidity to allow the part to be detached from the mold and handled without significant distortion or warping occurring. This allows for easier filling of the mold insert while avoiding a separate cooling step prior to removal of the part. Heating of the mold insert can be accomplished by any known conventional means, for example, by indirectly heating another part of the mold apparatus, such as the first mold member, and allowing the heat to transfer to the mold insert.

In another embodiment, the temperature of the mold insert 210 may be cycled so that it is at a higher temperature during the filling part of the cycle and at a lower temperature when the part is ejected. This so-called 'thermocycling' process may aid in filling and removal of the part. Additional details on thermocycling molding may be found in U.S. Patent Application Ser. No. 60/546,780 and U.S. Pat. No. 5,376,317 (Maus et al.), the disclosures of which are herein incorporated by reference.

Figure 5A:
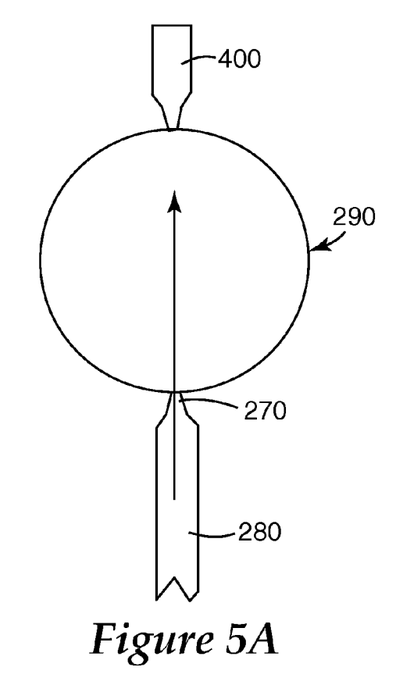
FIG. 5A is a schematic cross-sectional view of a detailed view of one embodiment of a mold apparatus.

In one embodiment, the mold apparatus includes an overflow vent 400 connected to the mold cavity 290, as shown in FIG. 5A. Molten polymeric material fed through the input line 280 passes through the injection gate 270 and into the mold cavity 290. The arrow shows the general direction of flow of polymeric material from the input line 280 into the mold cavity 290. As the polymeric material fills the mold cavity it displaces air that was in the cavity. In one embodiment, little or no displaced air becomes trapped in pockets within the mold cavity or within the negative images of microneedles in the mold insert.

Figure 5B:
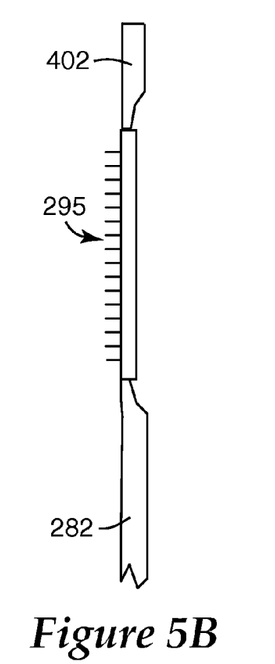
FIG. 5B is a schematic cross-sectional side view of polymeric material inside the detailed portion of the mold apparatus shown in FIG. 5A.

The overflow vent 400 serves as an exit gate to allow displaced air to leave the cavity thus allowing for more uniform filling of the mold cavity with polymeric material. The overflow vent may be positioned anywhere on the outer surface of the mold cavity. In one embodiment the overflow vent is positioned along the sidewalls of the mold cavity. In the embodiment shown in FIG. 5A, the overflow vent 400 is positioned along the sidewall and opposed to the injection gate 270. FIG. 5B shows a detailed side view of polymeric material 282 within the input line 280, polymeric material 402 within the overflow vent 400, and polymeric material in the form of a microneedle array 295 within the mold cavity 290.

A wide variety of polymeric materials may be suitable for use with the present invention. In one embodiment, the material is selected so that it is capable of forming relatively rigid and tough microneedles that resist bending or breaking when applied to a skin surface. In one aspect, the polymeric material has a melt-flow index greater than about 5 g/10 minutes when measured by ASTM D1238 at conditions of 300° C. and 1.2 kg weight. The melt-flow index is often greater than or equal to about 10 g/10 minutes and sometimes greater than or equal to about 20 g/10 minutes. In another embodiment, the tensile elongation at break as measured by ASTM D638 (2.0 in/minute) is greater than about 100 percent. In still another embodiment, the impact strength as measured by ASTM D256, "Notched Izod", (73° F.) is greater than about 5 ft-lb/ inches. Examples of suitable materials include polycarbonate, polyetherimide, polyethylene terephthalate, and mixtures thereof. In one embodiment the material is polycarbonate.

Although the compressive force is supplied by a wedge in the illustrated embodiment, any known conventional method of applying force may be used to provide compressive force to the mold cavity. The compression core may have any suitable shape that forms a major surface of the mold cavity and allows for application of compressive force to the material in the mold cavity. The compression core may be in the form of a piston or pin, and desirably the face of the piston or pin is the same diameter as the part to be formed. One skilled in the art would appreciate that many conventional methods for applying force may be utilized, such as, for example, using a hydraulic pancake cylinder.

Figure 6:
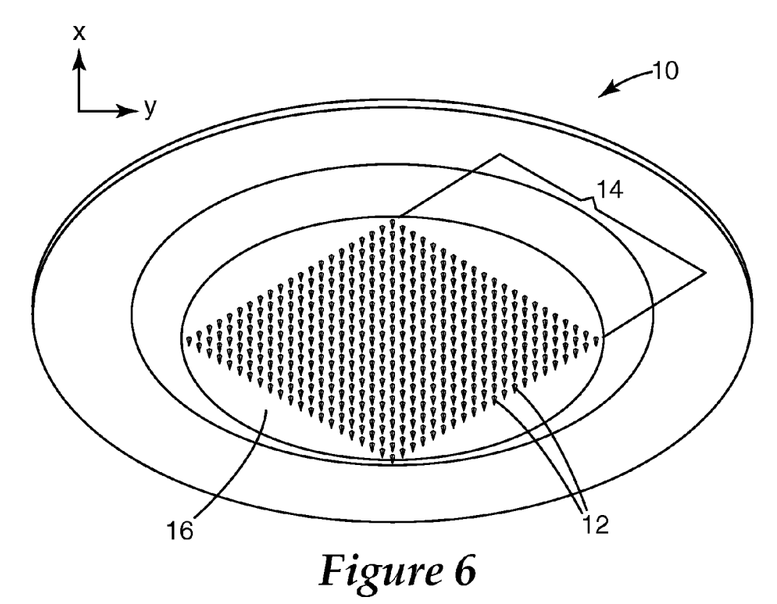
FIG. 6 is a schematic perspective view of a microneedle array.

In one embodiment of the present invention, microneedle arrays with molded microneedles integrally formed with a substrate may be prepared. FIG. 6 shows such a microneedle array 10. A portion of the array 10 is illustrated with microneedles 12 protruding from a microneedle substrate surface 16. The microneedles 12 may be arranged in any desired pattern 14 or distributed over the substrate surface 16 randomly. As shown, the microneedles 12 are arranged in uniformly spaced rows placed in a rectangular arrangement. In one embodiment, arrays of the present invention have a patient-facing surface area of more than about 0.1 cm$^2$ and less than about 20 cm$^2$, in some instances, more than about 0.5 cm$^2$ and less than about 5 cm$^2$. In the embodiment shown in FIG. 6, a portion of the substrate surface 16 is non-patterned. In one embodiment, the non-patterned surface has an area of more than about 1 percent and less than about 75 percent of the total area of the device surface that faces a skin surface of a patient. In one embodiment, the non-patterned surface has an area of more than about 0.10 square inch (0.65 cm$^2$) to less than about 1 square inch (6.5 cm$^2$). In another embodiment (not shown), the microneedles are disposed over substantially the entire surface area of the array 10. The thickness of the substrate surface may vary depending on the desired end use of the microneedle array. In one embodiment, the substrate surface may be less than 200 mil (0.51 cm) in thickness, often less than 100 mil (0.25 cm) in thickness, and sometimes less than 50 mil (0.13 cm) in thickness. The substrate surface is typically more than 1 mil (25.4 µm) in thickness, often more than 5 mil (127 µm) in thickness, and sometimes more than 10 mil (203 µm) in thickness.

The microneedles are typically less than 1000 microns in height, often less than 500 microns in height, and sometimes less than 250 microns in height. The microneedles are typically more than 20 microns in height, often more than 50 microns in height, and sometimes more than 125 microns in height.

The microneedles may be characterized by an aspect ratio. As used herein, the term "aspect ratio" is the ratio of the height of the microneedle (above the surface surrounding the base of the microneedle) to the maximum base dimension, that is, the longest straight-line dimension that the base occupies (on the surface occupied by the base of the microneedle). In the case of a pyramidal microneedle with a rectangular base, the maximum base dimension would be the diagonal line connecting opposed corners across the base. Microneedles of the present invention typically have an aspect ratio of between about 2:1 to about 5:1 and sometimes between about 2.5:1 to about 4:1.

The microneedle arrays prepared by methods of the present invention may comprise any of a variety of configurations, such as those described in the following patents and patent applications, the disclosures of which are herein incorporated by reference. One embodiment for the microneedle devices comprises the structures disclosed in U.S. Patent Application Publication No. 2003/0045837. The disclosed microstructures in the aforementioned patent application are in the form of microneedles having tapered structures that include at least one channel formed in the outside surface of each microneedle. The microneedles may have bases that are elongated in one direction. The channels in microneedles with elongated bases may extend from one of the ends of the elongated bases towards the tips of the microneedles. The channels formed along the sides of the microneedles may optionally be terminated short of the tips of the microneedles. The microneedle arrays may also include conduit structures formed on the surface of the substrate on which the microneedle array is located. The channels in the microneedles may be in fluid communication with the conduit structures. Another embodiment for the microneedle devices comprises the structures disclosed in co-pending U.S. patent application Ser. No. 10/621,620 filed on Jul. 17, 2003 which describes microneedles having a truncated tapered shape and a controlled aspect ratio. Still another embodiment for the microneedle arrays comprises the structures disclosed in U.S. Pat. No. 6,313,612 (Sherman, et al.) which describes tapered structures having a hollow central channel. Still another embodiment for the microneedle arrays comprises the structures disclosed in International Publication No. WO 00/74766 (Gartstein, et al.) which describes hollow microneedles having at least one longitudinal blade at the top surface of tip of the microneedle.

Figure 7:
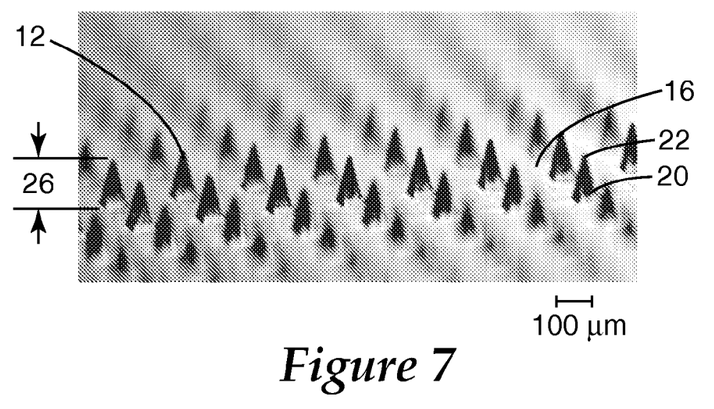
FIG. 7 is a microphotograph of a microneedle array.

Referring to FIG. 7, each of the microneedles 12 includes a base 20 on the substrate surface 16, with the microneedle terminating above the substrate surface in a tip 22. Although the microneedle base 20 shown in FIG. 7 is rectangular in shape, it will be understood that the shape of the microneedles 12 and their associated bases 20 may vary with some bases, e.g., being elongated along one or more directions and others being symmetrical in all directions. The base 20 may be formed in any suitable shape, such as a square, rectangle, or oval. In one embodiment the base 20 may have an oval shape (i.e., that is elongated along an elongation axis on the substrate surface 16).

One manner in which the microneedles of the present invention may be characterized is by height 26. The height 26 of the microneedles 12 may be measured from the substrate surface 16. It may be preferred, for example, that the base-to-tip height of the microneedles 12 be about 500 micrometers or less as measured from the substrate surface 16. Alternatively, it may be preferred that the height 26 of the microneedles 12 is about 250 micrometers or less as measured from the base 20 to the tip 22. It may also be preferred that the height of molded microneedles is greater than about 90%, and more preferably greater than about 95%, of the height of the microneedle topography in the mold insert. The microneedles may deform slightly or elongate upon ejection from the mold insert. This condition is most pronounced if the molded material has not cooled below its softening temperature, but may still occur even after the material is cooled below its softening temperature. It is preferred that the height of the molded microneedles is less than about 115%, and more preferably less than about 105%, of the height of the microneedle topography in the mold.

The general shape of the microneedles of the present invention may be tapered. For example, the microneedles 12 may have a larger base 20 at the substrate surface 16 and extend away from the substrate surface 16, tapering to a tip 22. In one embodiment the shape of the microneedles is pyramidal. In another embodiment, the shape of the microneedles is generally conical. In one embodiment the microneedles have a defined tip bluntness, such as that described in co-pending and commonly owned U.S. patent application Ser. No. 10/621,620, filed on Jul. 17, 2003 and entitled MICRONEEDLE DEVICES AND MICRONEEDLE DELIVERY APPARATUS, wherein the microneedles have a flat tip comprising a surface area measured in a plane aligned with the base of about 20 square micrometers or more and 100 square micrometers or less. In one embodiment, the surface area of the flat tip will be measured as the cross-sectional area measured in a plane aligned with the base, the plane being located at a distance of 0.98 h from the base, where h is the height of the microneedle above the substrate surface measured from base to tip.

Figure 3:
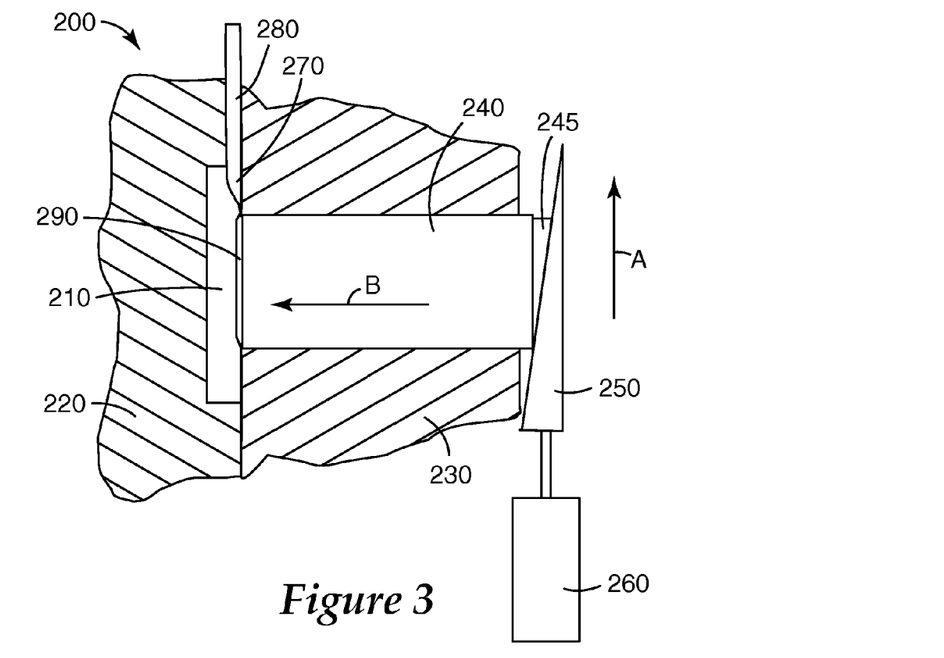
FIG. 3 is a schematic cross-sectional view of one embodiment of a mold apparatus in a compressed position.
Figure 4:
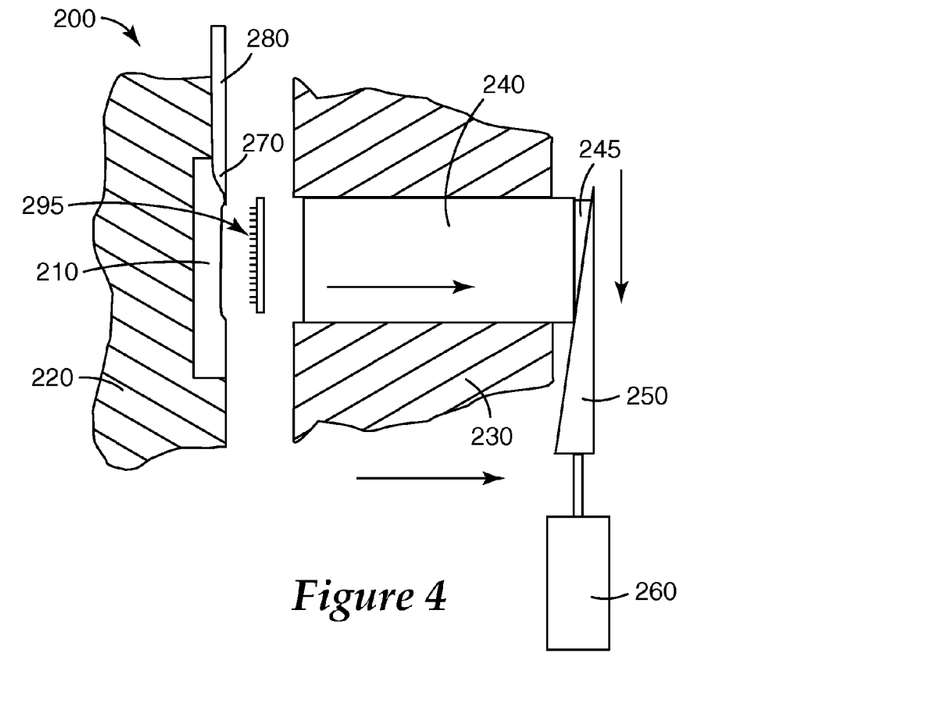
FIG. 4 is a schematic cross-sectional view of one embodiment of a mold apparatus in an open position with an ejected part.

The motion of the compression core 240 in FIGS. 2 and 3 is shown in an exaggerated fashion for purposes of illustration. In one embodiment, the bulk of the mold cavity 290 is substantially filled prior to compression and the compression step is performed largely to fill the negative images of microneedles 12 in the mold insert 210. The motion of the compression core is generally selected so as to displace a volume similar in size or larger than the volume of the mold cavity that remains unfilled by the initial injection step. In particular, it may be desirable to displace a larger volume in order to compensate for shrinkage of polymeric material in the mold cavity. Displacement of a larger volume may also be desirable in order to account for material that escapes the mold cavity as parting line flash or to account for mold plate deflections. The motion of the compression core and the resulting volume displaced may be adjusted depending on a number of parameters, including the size of the mold cavity, the shape and number of features in the mold cavity, the amount of the mold cavity filled by the initial injection step, and the type of material molded. Since the microneedle image(s) in the mold insert is relatively small both in height and volume, the motion of the compression core, that is the compression stroke, is typically between about 0.001 to 0.010 inches (25 μm to 250 μm), often between 0.002 to 0.008 inches (50 μm to 200 μm), and sometimes between 0.003 to 0.006 inches (75 μm to 150 μm).

The applied compressive force is typically greater than 5000 psi (34500 kPa), sometimes greater than 30000 psi (207000 kPa), and often greater than 60000 psi (414000 kPa). Additional details regarding injection-compression molding may be found in U.S. Pat. Nos. 4,489,033 (Uda et al.), 4,515, 543 (Hamner), and 6,248,281 (Abe et al.), the disclosures of which are herein incorporated by reference.

In one embodiment, the negative image(s) of the at least one microneedle is substantially completely filled with injected polymeric material prior to opening the mold and ejecting the part. By substantially completely filled, it should be understood that the molded microneedle should have a height greater than about 90 percent of the corresponding height of the microneedle topography in the mold insert. In one embodiment, the molded microneedle has a height greater than about 95 percent of the corresponding height of the microneedle topography in the mold insert. It is preferable that the molded microneedle has a height substantially the same (e.g., 95 percent to 105 percent) as the corresponding height of the microneedle topography in the mold insert.

Mold inserts suitable for use in the present invention may be made by any known conventional method. In one method, a positive 'master' is used to form the mold insert. The positive master is made by forming a material into a shape in which the microneedle array will be molded. This master can be machined from materials that include, but are not limited to, copper, steel, aluminum, brass, and other heavy metals. The master can also be made from thermoplastic or thermoset polymers that are compression formed using silicone molds. The master is fabricated to directly replicate the microneedle array that is desired. The positive master may be prepared by a number of methods and may have microneedles of any of a variety of shapes, for example, pyramids, cones, or pins. The protrusions of the positive master are sized and spaced appropriately, such that the microneedle arrays formed during molding using the subsequently formed mold insert have substantially the same topography as the positive master.

A positive master may be prepared by direct machining techniques such as diamond turning, disclosed in U.S. Pat. No. 5,152,917 (Pieper, et al.) and U.S. Pat. No. 6,076,248 (Hoopman, et al.), the disclosures of which are herein incorporated by reference. A microneedle array can be formed in a metal surface, for example, by use of a diamond turning machine, from which is produced a mold insert having an array of cavity shapes. The metal positive master can be manufactured by diamond turning to leave the desired shapes in a metal surface which is amenable to diamond turning, such as aluminum, copper or bronze, and then nickel plating the grooved surface to provide the metal master. A mold insert made of metal can be fabricated from the positive master by electroforming. These techniques are further described in U.S. Pat. No. 6,021,559 (Smith), the disclosure of which is herein incorporated by reference.

In another embodiment, the present invention comprises a method of molding microneedles whereby high frequency acoustic energy, such as ultrasonic energy, is applied to the mold apparatus 200. High frequency acoustic energy, such as ultrasonic energy, is applied to aid in preventing the injected polymer material from hardening against the face of the mold insert before cavity pressure and compression stroke forces the material into the mold cavity. In one embodiment, ultrasonic energy is applied to the mold insert 210 or input line in conjunction with the combination of injection and compression molding, for example, as illustrated in FIGS. 1 to 4. In one embodiment, the use of ultrasonic energy prevents the polymeric material from substantially cooling before filling the narrow channels, since the polymeric material can be prone to "skin over" or solidify in the channel prior to complete filling and thus block further flow of molten material. The compressive force used in conjunction with ultrasonic energy is typically greater than 2000 psi (13800 kPa), often greater than 5000 psi (34500 kPa), and sometimes greater than 10000 psi (69000 kPa).

Figure 8:
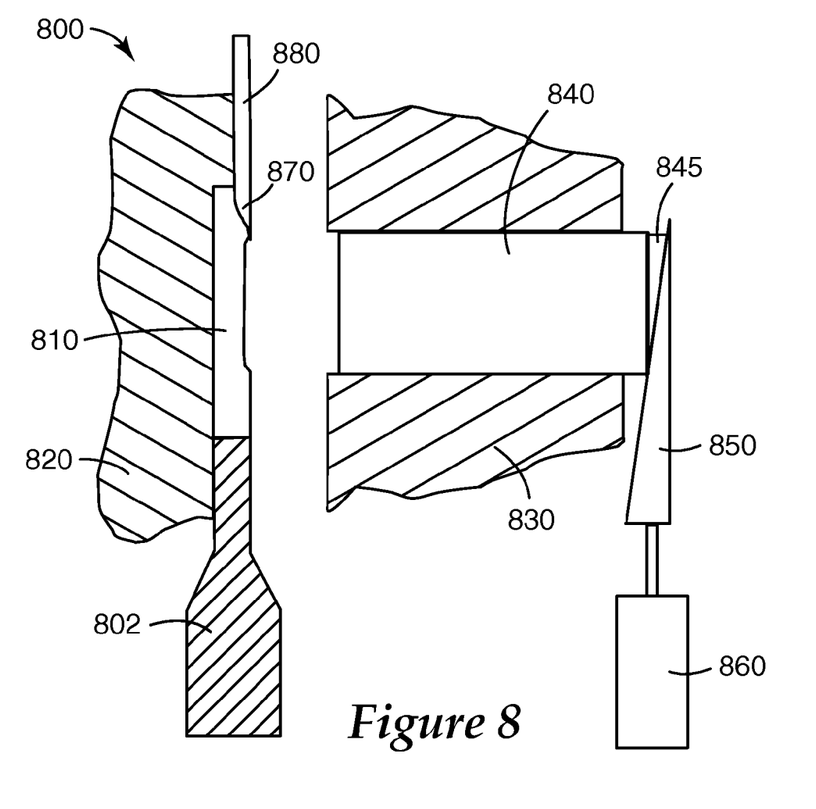
FIG. 8 is a schematic cross-sectional view of another embodiment of a mold apparatus.

Referring to FIG. 8, an ultrasonic horn 802 may be placed up against one side of the mold insert 810. The first mold member 820 supports the horn 802, the mold insert 810 and the input line 880. The second mold member 830 is used as described above. Ultrasonic energy from the horn 802 may be applied at any time while the mold apparatus is in the closed position, such as during the step of injecting polymeric material or during the step of compressing the injected polymeric material. In one embodiment, ultrasonic energy is initially applied after the start of the step of injecting polymeric material. In one embodiment, ultrasonic energy is initially applied before the compressing step. The application of ultrasonic energy is preferably stopped before the mold apparatus is opened. In one embodiment, the ultrasonic energy may be applied for a time period of about 0.5 to 5 seconds and sometimes for a time period of about 0.5 to 2 seconds.

Figure 9A:
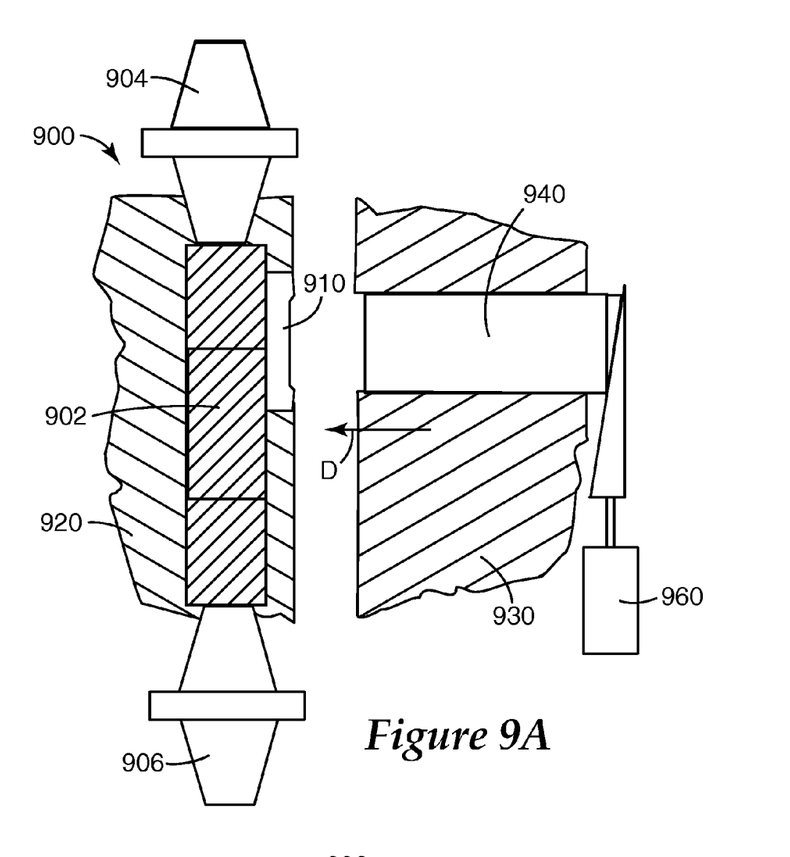
FIG. 9A is a schematic cross-sectional view of still another embodiment of a mold apparatus.
Figure 9B:
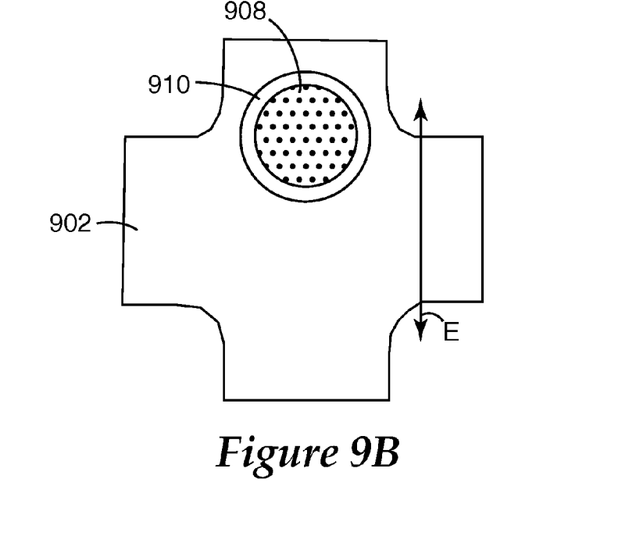
FIG. 9B is a side view of a portion of the mold apparatus shown in FIG. 9A.
Figure 10:
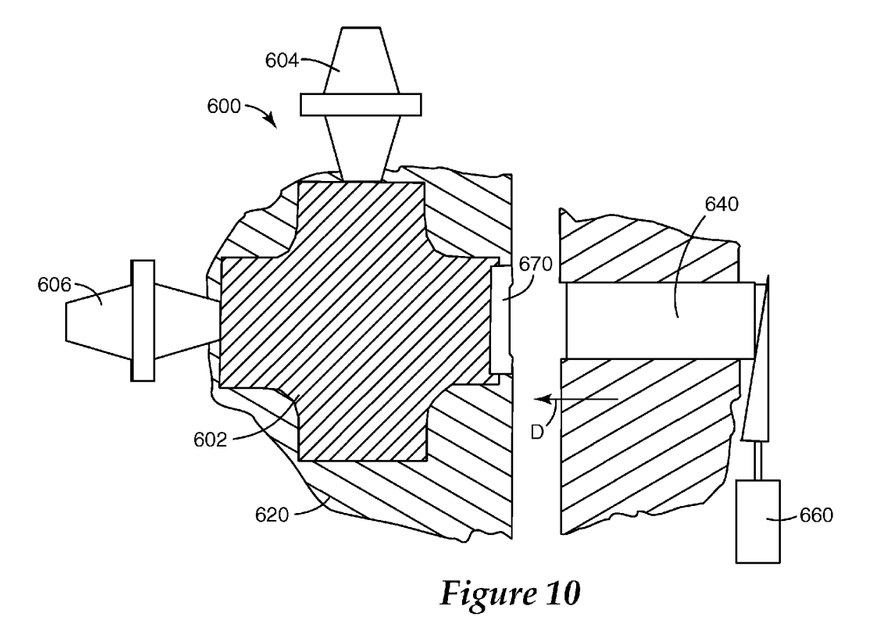
FIG. 10 is a schematic cross-sectional view of still another embodiment of a mold apparatus.

In another embodiment, the ultrasonic horn 902 in FIGS. 9A, B is shown as a flat, cross-shaped member. Ultrasonic boosters 904, 906 are coupled to opposing sides of the ultrasonic horn 902. The mold insert 910 is shown positioned such that it is placed over one "lobe" of the cross-shaped horn. The application of power from the boosters 904, 906 causes application of energy in a direction of shear across the face of the mold insert 908 as shown by the two-sided arrow labelled E in FIG. 9B. As shown, the face of the ultrasonic horn 902 makes a flush contact with the back surface of the mold insert 910. Alternatively, the mold insert 910 may be partially or fully recessed into the surface of the ultrasonic horn 902 (as is shown in FIG. 10). The remainder of the mold apparatus is operated as described above. The mold apparatus 900 would also have one or more input lines and injection gates (not shown) suitable for introducing polymeric material into the mold cavity that is formed when the apparatus 900 is placed into a closed position. Ultrasonic energy from the horn 902 may be applied during the step of injecting polymeric material or during the step of compressing the injected polymeric material. The application of ultrasonic energy may be stopped before the mold apparatus is opened.

In still another embodiment, the ultrasonic horn 602 may be a flat, cross-shaped member aligned as shown in FIG. 10. The mold insert 670 is shown partially recessed into one surface of the ultrasonic horn 602. The ultrasonic boosters 604, 606 are shown aligned on adjacent sides of the ultrasonic horn 602. A converter (not shown) is coupled to booster 606 to drive ultrasonic vibration along an axis parallel to the length of the microneedle cavities. The remainder of the mold apparatus is operated as described above. Ultrasonic energy from the horn 602 may be applied during the step of injecting polymeric material or during the step of compressing the injected polymeric material. The application of ultrasonic energy may be stopped before the mold apparatus is opened.

Figure 11A:
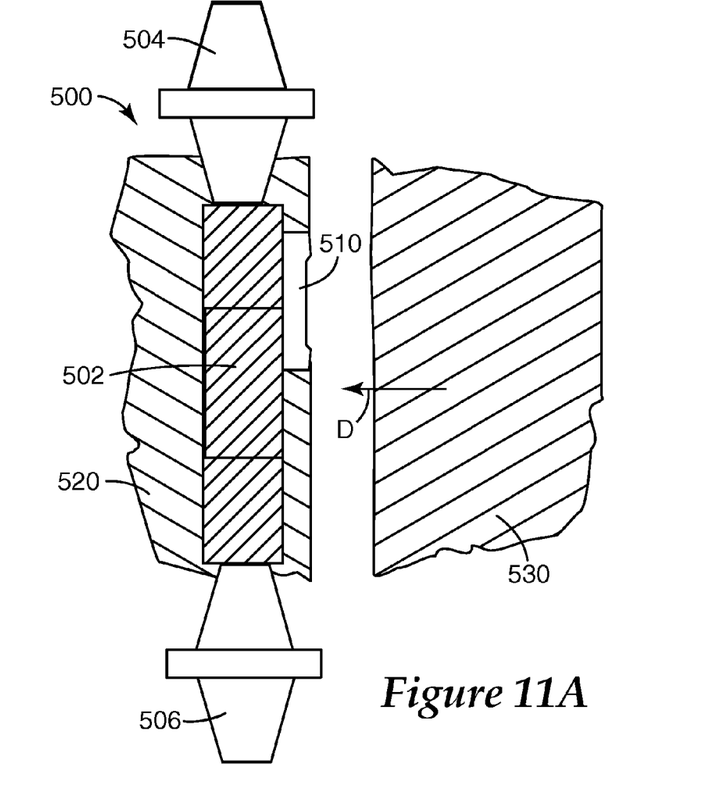
FIG. 11A is a schematic cross-sectional view of still another embodiment of a mold apparatus.
Figure 11B:
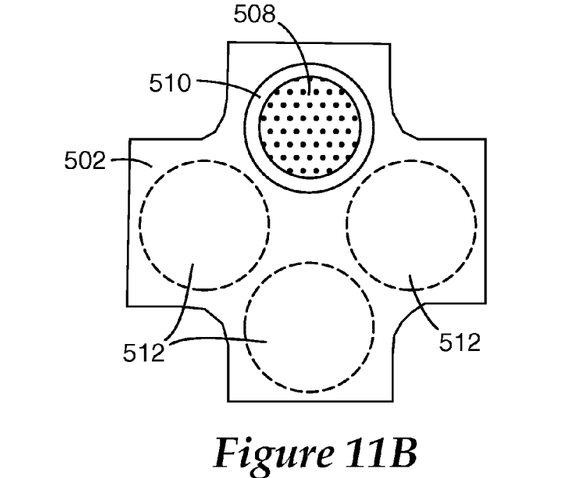
FIG. 11B is a side view of a portion of the mold apparatus shown in FIG. 11B.

In this and the foregoing embodiments, the arrangement of ultrasonic boosters may be varied, for example, by placing boosters against each lobe of the ultrasonic horn that does not contact the mold insert, or by placing boosters against other surfaces of the ultrasonic horn. The ultrasonic horn may have any of a number of other conventional shapes suitable for transmitting ultrasonic energy to the mold apparatus. For example, a stepped cylinder (as shown in FIG. 8), a stepped bar, or a rectangular bar may be used. Ultrasonic energy may be applied in a direction parallel to the plane of the microneedle array, perpendicular to the plane of the microneedle array, or at some other angle with respect to the microneedle array. In one embodiment, a solid second mold member 530 (shown in FIG. 11A) may be used to press up against the first mold member 520, thereby forming a mold cavity along with the mold insert 510. The ultrasonic horn 502 and boosters 504, 506 are used as described above to facilitate filling of injected polymeric material into the mold insert. The mold insert 510 is shown positioned such that it is placed over one "lobe" of the cross-shaped horn. The first mold member 520 and second mold member 530 may be optionally configured so that multiple mold inserts may be held in place against the ultrasonic horn 502. FIG. 11B shows where three optional mold inserts 512 may be placed against the horn 502. The mold apparatus 500 would also have one or more input lines and injection gates (not shown) suitable for introducing polymeric material into the mold cavity that is formed when the apparatus 500 is placed into a closed position. Placement of two or more mold inserts against the ultrasonic horn could be employed in any of the foregoing embodiments taking into account the size of the mold inserts and the size of the ultrasonic horn. In embodiments where a compression core is employed it may be advantageous to use an individual compression core in conjunction with each mold insert or alternatively a single compression core may be sized and gated appropriately to simultaneously provide compressive force to more than one mold insert.

The ultrasonic energy used may vary in frequency, but is typically defined as having a frequency greater than or equal to about 20,000 Hz. Although any ultrasonic frequency may be used, it will typically be less than 60,000 Hz, often less than 40,000 Hz, and sometimes less than 30,000 Hz. In one embodiment, the frequency is about 20,000 Hz. Although the specific embodiments of FIGS. 8 to 11 described above refer to ultrasonic energy, relatively high frequency acoustic energy with a frequency greater than about 5,000 Hz is also suitable to provide vibrational energy to aid in filling the narrow channels of the mold insert. In one embodiment, the acoustic energy has a frequency of between about 10,000 Hz and 60,000 Hz, often between about 15,000 Hz and 40,000 Hz.

Ultrasonic energy may be applied using an ultrasonic horn. The amplitude of motion of the ultrasonic horn is typically less than about 0.005 inch (127 μm) and is often less than about 0.002 inch (51 μm). In one embodiment, the amplitude of motion of the ultrasonic horn may be between about 0.0005 inch (12.7 μm) and 0.0015 inch (38.1 μm). The ultrasonic energy is generally supplied by using a power source that supplies electrical energy of the desired frequency. Power sources will typically provide from 500 to 3000 W power. The electrical energy is fed to a converter or transducer which transforms the electrical energy into mechanical energy with the same frequency. The mechanical vibrations are then amplified or boosted and transmitted by the ultrasonic horn.

The ultrasonic horn is situated with respect to the mold apparatus so that vibrational energy is transmitted to the mold apparatus. It may be desirable, for example, for the ultrasonic horn to be in direct contact with a portion of the mold apparatus, such as the mold insert. The apparatus may be configured so that the ultrasonic horn is simply held against the mold insert or the ultrasonic horn may be physically connected to the mold insert by any conventional means. In one embodiment, the ultrasonic horn may be welded or glued directly to the mold insert. In another embodiment, the ultrasonic horn may have a recessed opening into which the mold insert can be press-fit. Alternatively, the mold insert can be chilled, thus causing a dimensional contraction, placed into a recessed opening in the horn, and then allowed to warm and expand, thus causing a firm attachment. In one embodiment, the ultrasonic horn and mold insert may be connected to each other by an intermediate member. Such an intermediate member is desirably selected so as to efficiently transfer ultrasonic energy from the horn to the mold insert. In another embodiment, the ultrasonic horn may comprise part or all of the face of the mold opposed to the mold insert, such that the ultrasonic horn directly contacts the injected polymeric material.

In another embodiment, the present invention is a method of molding a microneedle using a mold apparatus that comprises a mold insert having the negative image of at least one microneedle, a compression core, and a mold housing configured to allow a reciprocal motion between the mold insert and the compression core. The mold apparatus has an open position and a closed position. The mold apparatus is placed in the closed position and polymeric material is injected into the closed mold apparatus. The injected polymeric material is compressed between the mold insert and the compression core by a reciprocal motion between the compression core and the mold insert. The mold is opened and a molded microneedle is removed from the mold. The polymeric material is injected into the mold apparatus through an injection gate. The injection gate may be along the sidewalls of the mold cavity (i.e., side gated) or it may be aligned along a major surface of the mold cavity (i.e., center gated). Examples of suitable injection gates include a hot tip gate, a valve gate, a tab gate, a tunnel gate, a cashew gate, and a cold 3-plate pin gate.

Microneedle arrays prepared by methods of the present invention may be suitable for delivering drugs (including any pharmacological agent or agents) through the skin in a variation on transdermal delivery, or to the skin for intradermal or topical treatment, such as vaccination.

In one aspect, drugs that are of a large molecular weight may be delivered transdermally. Increasing molecular weight of a drug typically causes a decrease in unassisted transdermal delivery. Microneedle devices suitable for use in the present invention have utility for the delivery of large molecules that are ordinarily difficult to deliver by passive transdermal delivery. Examples of such large molecules include proteins, peptides, nucleotide sequences, monoclonal antibodies, DNA vaccines, polysaccharides, such as heparin, and antibiotics, such as ceftriaxone.

In another aspect, microneedle arrays prepared by methods of the present invention may have utility for enhancing or allowing transdermal delivery of small molecules that are otherwise difficult or impossible to deliver by passive transdermal delivery. Examples of such molecules include salt forms; ionic molecules, such as bisphosphonates, preferably sodium alendronate or pamedronate; and molecules with physicochemical properties that are not conducive to passive transdermal delivery.

In another aspect, microneedle arrays prepared by methods of the present invention may have utility for enhancing delivery of molecules to the skin, such as in dermatological treatments, vaccine delivery, or in enhancing immune response of vaccine adjuvants. In one aspect, the drug may be applied to the skin (e.g., in the form of a solution that is swabbed on the skin surface or as a cream that is rubbed into the skin surface) prior to applying the microneedle device.

Microneedle devices may be used for immediate delivery, that is where they are applied and immediately removed from the application site, or they may be left in place for an extended time, which may range from a few minutes to as long as 1 week. In one aspect, an extended time of delivery may be from 1 to 30 minutes to allow for more complete delivery of a drug than can be obtained upon application and immediate removal. In another aspect, an extended time of delivery may be from 4 hours to 1 week to provide for a sustained release of drug.

EXAMPLES

Example 1

Molded microneedle arrays were prepared using a 55-ton injection molding press (Milacon Cincinnati ACT D-Series Injection Molding Press) equipped with a thermocycling unit (Regoplas 301 DG Thermal Cycling Unit) in an apparatus as generally shown in FIGS. 1 to 4. Polycarbonate pellets (Lexan® HPS1R-1125, GE Plastics, Pittsfield, Mass.) were loaded into a reciprocating screw and heated until molten. The negative mold insert was heated to a temperature (hereafter referred to as the "mold temperature at injection") of 340° F. (171.1° C.). The mold insert was shaped to provide a microneedle array having a substrate in the shape of a circular disk with an area of 2 cm². The mold insert was partially patterned with cavities in the form of the negative image of an array of microneedles (37×37) in a square shape (1 cm²) in the center of the circular disk. The microneedle cavities were regularly spaced with a distance of 275 microns between the tips of adjacent microneedle cavities in a square-shaped pattern. Individual microneedle cavities were pyramidal in shape with a depth of 250 microns and a square opening having a side-length of 83.3 μm. The tips were truncated with a flat, square-shaped top having a side-length of 5 μm. The molding cycle was initiated by closing the mold chamber, clamping the mold with 55 tons of force, and injecting a first portion (approx. 50-95% of the part size volume) of the total amount of material from the reciprocating screw into the negative mold insert. The first portion of material was injected into the negative mold insert at a fixed velocity (hereafter referred to as the "injection velocity") of 0.50 in/sec (1.27 cm/sec). After injecting the first portion of material the process was switched from an injection-driven to a pressure-driven mode by applying a fixed pressure (hereafter referred to as the "pack pressure") of 12000 psi (81.6 MPa) to force the remainder of the molten material into the negative mold insert. The pack pressure was applied for a fixed time (hereafter referred to as the "hold time") of 4 seconds. The piston was initially positioned so that the height of the mold chamber (measured from face of the piston to face of the mold insert) was 30 mil (762 μm). Compression was applied by moving the piston a distance of 5 mil (127 μm) towards the opposite side of the microneedle cavity in order to compress the molten material into the microneedle cavities. The pack pressure was subsequently released and the negative mold insert was cooled to an ejection temperature (hereafter referred to as the "mold temperature at ejection") of 250° F. (121.1° C.). Then the mold chamber was opened and a microneedle array was ejected. The average microneedle height thus formed was 250 μm as measured by viewing with a stereomicroscope.

Example 2

Microneedle arrays were prepared as in Example 1 with the following exceptions. The second mold member had a fixed face and thus no compression step was used (i.e., as shown in FIG. 11A). The mold temperature at injection and the mold temperature at ejection were both 200° F. (93.3° C.), that is, the mold temperature remained constant. Ultrasonic energy was applied to the mold insert as generally shown in FIG. 10. The ultrasonic energy was turned on before application of the pack pressure (approximately 0.5 second after the onset of injection of molten material) and was applied for approximately 1.0 second. The frequency was 20,000 Hz and the amplitude of motion of the ultrasonic horn was 1.5 mil (38.1 μm). The average microneedle height thus formed was 240 μm as measured by viewing with a stereomicroscope.

Example 3

Microneedle arrays were prepared as in Example 1 with the following exceptions. The mold temperature at injection and the mold temperature at ejection were both 200° F. (93.3° C.), that is, the mold temperature remained constant. Ultrasonic energy was applied to the mold insert as generally shown in FIG. 10. The ultrasonic energy was turned on before application of the pack pressure (approximately 0.5 second after the onset of injection of molten material) and was applied for approximately 1.0 second. The frequency was 20,000 Hz and the amplitude of motion of the ultrasonic horn was 1.5 mil (38.1 μm). The average microneedle height thus formed was 245 μm as measured by viewing with a stereomicroscope.

The present invention has been described with reference to several embodiments thereof. The foregoing detailed description has been provided for clarity of understanding only, and no unnecessary limitations are to be understood therefrom. It will be apparent to those skilled in the art that many changes can be made to the described embodiments without departing from the spirit and scope of the invention. Thus, the scope of the invention should not be limited to the exact details of the methods and structures described herein, but rather by the language of the claims that follow.

We claim:

1. A method of molding a microneedle array comprising:
    (i) providing a mold apparatus comprising:
        a mold insert having the negative image of at least one microneedle;
        a compression core; and
        a mold housing configured to allow a reciprocal motion between the mold insert and the compression core,
        wherein the mold apparatus has an open position and a closed position;
    (ii) placing the mold apparatus in the closed position;
    (iii) applying acoustic energy having a frequency greater than about 5,000 Hz to the mold apparatus;
    (iv) injecting polymeric material into the closed mold apparatus;
    (v) compressing the injected polymeric material between the mold insert and the compression core by a reciprocal motion between the compression core and the mold insert;
    (vi) opening the mold; and
    (vii) removing the molded microneedle from the mold.

2. A method as claimed in claim 1 wherein the acoustic energy is ultrasonic energy that is applied to the mold insert.

3. A method as claimed in claim 1, wherein the polymeric material is polycarbonate.

4. A method as claimed in claim 1 wherein the compressive force applied to the mold cavity during the compressing step is greater than 5000 psi (34500 kPa).

5. A method as claimed in claim 1 wherein the mold insert has the negative image of a plurality of microneedles in the form of an array.

6. A method as claimed in claim 5 wherein the mold insert has the negative image of a plurality of arrays.

7. A method as claimed in claim 5 wherein the molded microneedle is formed as part of a microneedle array comprising a plurality of microneedles integrally formed with a substrate.

8. A method as claimed in claim 5, wherein the microneedle array comprises a plurality of molded microneedles having a height greater than about 95 percent of the corresponding height of the microneedle topography in the mold insert.

9. A method as claimed in claim 7 wherein the acoustic energy is applied in a direction perpendicular to the plane of the microneedle array.

10. A method as claimed in claim 7 wherein the acoustic energy is applied in a direction parallel to the plane of the microneedle array.

11. A method as claimed in claim 1 wherein the acoustic energy is applied by an ultrasonic horn.

12. A method as claimed in claim 11 wherein the ultrasonic horn directly contacts the injected polymeric material.

13. A method as claimed in claim 11 wherein the ultrasonic horn is cross-shaped.

* * * * *

UNITED STATES PATENT AND TRADEMARK OFFICE
CERTIFICATE OF CORRECTION

PATENT NO. : 8,246,893 B2
APPLICATION NO. : 13/049448
DATED : August 21, 2012
INVENTOR(S) : Dennis E. Ferguson et al.

It is certified that error appears in the above-identified patent and that said Letters Patent is hereby corrected as shown below:

Title Page 2, Column 2, under OTHER PUBLICATIONS
Line 1, "moldling" should read --molding--.
Line 19, "Pastics" should read --Plastics--.
Line 25, "XP00446148." should read --XP000446148.--.

Column 3
Line 29, "11B." should read --11A.--.

Column 12
Line 17, "pamedronate;" should read --pamidronate;--.
Line 44, "Milacon" should read --Milacron--.
Line 46, "Regoplas" should read --Regloplas--.

Signed and Sealed this
Twenty-sixth Day of February, 2013

Teresa Stanek Rea
*Acting Director of the United States Patent and Trademark Office*